United States Patent [19]

Carr et al.

[11] 4,202,902

[45] May 13, 1980

[54] LIPOGENESIS CONTROL BY CYCLOPROPANE-CARBOXYLIC ACIDS, ESTERS AND AMIDES

[75] Inventors: John B. Carr, Houston, Tex.; Harry G. Durham, Modesto, Calif.

[73] Assignee: Shell Oil Company, Houston, Tex.

[21] Appl. No.: 17,214

[22] Filed: Mar. 5, 1979

[51] Int. Cl.$^2$ .................. A61K 31/22; A61K 31/275; A61K 31/215; A61K 31/16

[52] U.S. Cl. .................................... 424/298; 424/304; 424/305; 424/320

[58] Field of Search ............... 424/304, 298, 305, 320; 260/464

[56] References Cited

U.S. PATENT DOCUMENTS

| | | | |
|---|---|---|---|
| 3,989,722 | 11/1976 | Cognacq | 424/304 |
| 4,080,474 | 3/1978 | Hindley et al. | 424/304 |

OTHER PUBLICATIONS

Senior et al., Chem. Abs., 1966, vol. 65, p. 19168.
Senior et al., Chem. Abs., 1967, vol. 67, p. 107062g.
Duncombe et al., Chem. Abs., 1968, vol. 69, p. 94244g.

*Primary Examiner*—Dale R. Ore

[57] ABSTRACT

Lipogenesis in mammals is inhibited by certain cyclopropanecarboxylic acids, esters and amides.

1 Claim, No Drawings

LIPOGENESIS CONTROL BY CYCLOPROPANE-CARBOXYLIC ACIDS, ESTERS AND AMIDES

DESCRIPTION OF THE INVENTION

It has been found that lipogenesis in mammals is inhibited by cyclopropanecarboxylic acids, esters and amides, which are described by the formula:

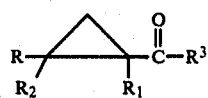

consisting of two subclasses (1) R is $C_4$-$C_{10}$ alkyl, acetoxymethyl, or phenyl, $R^1$ and $R^2$ each is hydrogen or -CN, with the proviso that one of them is hydrogen, and $R^3$ is $-NH_2$, or $-OR^4$, wherein $R^4$ is $C_1$-$C_4$ alkyl;

(2) R is $C_6$-$C_{16}$ alkyl, or is phenyl, $R^1$ and $R^2$ each is hydrogen or —CN, with the proviso that one of them is hydrogen and $R^3$ is —OH.

In these compounds, each alkyl moiety suitably can be of either straight-chain or branched-chain configuration.

Some of the compounds are known in the art.

For illustration, preparation of typical individual species of the compounds defined by Formula I are described in the examples included hereinafter.

The esters of Formula I wherein $R^1$ is hydrogen can be prepared by the method described by A. P. Meshcheryakov and I. E. Dolgii, Izvest. Akad. Nauk S.S.S.R., Otdel. Khim. Nauk, 931-934 1960, (Chem. Abst. 54, 24436d (1954)): the appropriate 1-olefin is treated with the appropriate ester of diazoacetic acid in the presence of a small amount of copper sulfate. The article by K. Hofmann, et al., J. Am. Chem. Soc., 76, 1799-1804 (1954), also is pertinent to this method.

The esters of Formula I wherein $R^1$ is —CN can be prepared by the method of E. W. Yankee, et al., J. Am. Chem. Soc., 95, 4220-4230 (1973): the appropriate alkyl 2-cyanocinnamate (J. Zabicky, J. Chem. Soc., 1961, 683-7) is treated with dimethyloxosulfonium methylide (sodium hydride+trimethylsulfoxonium iodide) in dimethyl sulfoxide.

The amides of Formula I ($R^2$ is $-NH_2$) can be prepared by treating the appropriate alkyl ester with [LiAlH(NH₂)₂]₂NH, as described by J. Petit and R. Poisson, Compt, rend., 247, 1628-30 (1958) (Chem. Abst. 53, 10025t (1959)).

The acids of Formula I can be prepared by conventional hydrolysis of the appropriate esters.

Procedures for preparing compounds of Formula I are illustrated in the following examples. In each case, the identity of the product, and of any precursor(s) involved, was confirmed by the appropriate elemental and spectral analyses.

EXAMPLE 1

Ethyl 2-octylcyclopropanecarboxylate (trans) (1)

A mixture of 60 g of ethyl diazoacetate and 100 g of decene was added drop-by-drop to a stirred suspension of 4 g of anhydrous copper sulfate in 700 g of decene, at 105° C. The addition required 1.5 hours. The mixture was stirred for an additional 2 hours, then filtered, and the filtrate was distilled, to give 1, as a liquid, bp: 107°-110° C. (0.1 Torr.).

EXAMPLES 2 AND 3

By the general procedure described in Example 1:

Ethyl 2-nonylcyclopropanecarboxylate (trans-) (2) was prepared as a liquid, bp: 105°-106° C. (0.1 Torr.).

Ethyl 2-butylcyclopropanecarboxylate (3) was prepared as a liquid, bp: 105°-110° C. (25 Torr.).

EXAMPLE 4

2-Octylcyclopropanecarboxamide (trans) (4)

4 g of lithium aluminum hydride was mixed with 300 ml of dry ether under a nitrogen blanket. Gaseous ammonia was liquefied by a dry ice condenser and the liquefied ammonia was dripped over a period of one hour onto the hydride/ether mixture until no further evolution of hydrogen was observed (7 g of ammonia used). 22.6 g of 1 was added drop-by-drop over a period of one hour and the resulting solution was stirred for 3 hours at 30° C., then poured into a mixture of 500 ml of 5% sulfuric acid and 200 g of ice. The ether layer was separated and the aqueous layer was extracted with ether. The ether layer and extracts were combined and the ether was evaporated. The residue was recrystallized from hot hexane, then from cold methanol, to give 4, as a solid, mp: 109°-110° C.

EXAMPLE 5

2-Nonylcyclopropanecarboxylic acid (trans) (5)

A mixture of 36 g of 2, 8 g of sodium hydroxide and 100 ml of ethanol was heated on a steam bath for 2 hours. The alcohol was evaporated under reduced pressure. The residue was dissolved in 300 ml of hot water. The solution was made acid with 6 N hydrochloric acid. The oil layer which formed was taken up in pentane. The solution was filtered, and the pentane was evaporated. The product was distilled to give 5, as a pale yellow liquid, bp: 168°-170° C. (0.1 Torr.).

EXAMPLES 6 and 7

By the general procedure described in Example 5:

2-octylcyclopropanecarboxylic acid (trans) (6) was prepared from 1, as a liquid, bp: 158°-161° C. (1.2 Torr.).

2-tetradecylcyclopropanecarboxylic acid (trans) (mp: 62°-64° C.) (7) was prepared from the corresponding ethyl ester, which was prepared by the general procedure described in Example 1.

EXAMPLE 8

2-Nonylcyclopropanecarboxycarboxamide (trans) (8)

20 g of 5, prepared as described in Example 5, was heated in a steam bath with 20 ml of thionyl chloride for 1 hour. The resulting mixture was stripped under reduced pressure. The residue was poured onto concentrated ammonium hydroxide at -10° C. The mixture was warmed on a steam bath. The solid was filtered, recrystallized from hexane, and then from cold methanol, to give 8, as a solid, mp: 95°-6° C.

EXAMPLE 9

Ethyl 1-cyano-2-phenylcyclopropanecarboxylate (9)

A mixture of 7.9 g of sodium hydride in 7.9 g of mineral oil was washed with hexane under a nitrogen blanket. The hexane was decanted, 35.7 g of trimethylsulfoxonium iodide was added at 20° C. with stirring, then 65 ml of dimethyl sulfoxide was added, with cooling, to hold the mixture at about 20° C. The resulting slurry was cooled to 10° C. and a solution of 30 g of ethyl 1-cyanocinnamate in 75 ml of dimethyl sulfoxide was added over a one-hour period, at 10°–15° C. The mixture then was stirred at 25° C. for 1 hour, then at 40°–50° C. for 2 hours. The mixture was added to 300 g of ice and 400 ml of ether. The ether layer was separated, washed with saturated sodium chloride solution, and the ether was evaporated under reduced pressure. The residue was extracted with hot hexane, and the hexane was evaporated under vacuum to give two liquid phases. The oil phase was separated to give 9, as a cloudy liquid, bp: 130°–132° C. (0.1 Torr.).

EXAMPLE 10

Ethyl 1-cyano-2-hexylcyclopropanecarboxylate (trans-) (10)

10 was prepared as a liquid, boiling point not determined, from ethyl 2-cyano-2-nonenoate (M. Igarashi and H. Midorikawa, J. Org. Chem. 28, 3088–92 (1963); F. D. Popp and A. Catala, J. Org. Chem., 26, 2738–40 (1961)), by the method described in Example 9.

EXAMPLE 11

1-Cyano-2-phenylcyclopropanecarboxylic acid (11), can be prepared as a solid, mp: 137°–138° C., by treating 9 according to the general procedures described in Example 5.

EXAMPLE 12

Ethyl 2-((acetyloxy)methyl)cyclopropanecarboxylate (12)

12 was prepared, as a liquid, bp: 94°–95° C. (0.02 Torr.), from allyl acetate according to the procedure described in Example 1.

EXAMPLE 13

2-phenylcyclopropane-1-carboxylic acid (trans) (13) was purchased from Aldrich Chemical Company.

EXAMPLE 14

Ethyl 2-cyano-2-phenylcyclopropanecarboxylate (14)

Atroponitrile (14 A) was prepared by a literature procedure (J. Org. Chem., 21, 635 (1956). A 13 g portion of 14 A was added to a solution of 15 g of ethyl(-dimethylsulfuranylidene)acetate (J. Org. Chem., 32, 3351–5 (1967)) in 50 ml of benzene, at room temperature. The temperature of the mixture rose to 37° C. The resulting mixture was allowed to stand at room temperature over a weekend. Result: a very dark mixture, with some oily insoluble material deposited in the walls of the flask. The mixture was decanted and Claisen distilled to give 14, as a liquid boiling at 120°–125° C. at 1 Torr. pressure.

The compounds of Formula I have been found to inhibit lipogenesis in tissues of mammals. The manner in which they cause this effect is not known with certainty; it is believed that they interfere with the synthesis of fatty acids in the tissue. Their effectiveness for this purpose has been ascertained by immersing samples of swine adipose tissue in a liquid medium containing radioactive glucose and the test chemical for a period time, then isolating the lipid from the treated tissue and determining the incorporation of the ratioactive carbon into the lipid by means of scintillation counting techniques. These tests were conducted in swine adipose tissue because in swine the primary site of lipogenesis—i.e., fatty acid synthesis—appears to be adipose tissue.

Described in more detail, the tests were conducted according to the following general procedure.

150 milligrams of slices of swine adipose tissue were incubated at 37° C. for 2 hours with shaking in 3 milliliters of Krebs-Ringer bicarbonate solution containing one-half the usual calcium ion concentration, 60 micromoles of glucose, 0.5 microCurie of glucose-U$^{14}$C, and 100 milliunits of insulin, and 5% dimethyl sulfoxide (DMSO). The test compounds were added as a solution or suspension in DMSO and were present at a concentration of 100 micrograms per milliliter of the incubation mixture.

The incubation was terminated by addition of 0.25 milliliter of 1 N sulfuric acid. The resulting mixture was extracted with a total of 25 milliliters of chloroform:methanol (2:1 v/v). The extracts were washed according to Folch et al. (J. Biol. Chem., 226, 497–509, (1957)), air dried, and counted in a liquid scintillation counter with 15 milliliters of counting fluid (two parts toluene containing 0.4% w/v New England Nuclear Omnifluor: 1 part Triton X-100). The tests were conducted in triplicate and were accompanied by control tests in which all ingredients, proportions and conditions were the same except that no test compound was included. From the data obtained were calculated the percent inhibition of lipid synthesis by the test compound in each case. The data obtained from these tests were set out in Table I, as the percent inhibition of lipogenesis compared to the results obtained in the control tests wherein only the test compound was omitted.

Table I

| Compound No. | Percent Inhibition |
|---|---|
| 1 | >20 |
| 2 | 27 |
| 3 | 24 |
| 4 | >20 |
| 5 | 79 |
| 6 | 77 |
| 7 | 46 |
| 8 | 34 |
| 9 | 57 |
| 10 | 44 |
| 11 | 49 |
| 12 | 31 |
| 13 | 32 |
| 14 | 53 |

Compounds 1 and 6 were tested to determine the in vivo inhibition of swine adipose tissue lipid synthesis, as follows: pigs weighing about 20 kilograms were administered a fixed drug dose of approximately 25 milligrams of drug per kilogram of animal body weight per day for seven consecutive days. The drug was formulated to contain 10%w active ingredient and was prepared as coarse granules using 4%w plasdene as the granulating agent and lactose as the carrier. Control animals received a comparable amount of lactose as a placebo. The daily drug or placebo dose was added to 1.2 kilograms of swine ration; about one-third of the total was fed at 0800, 1200, and 1600 hours. Biopsy samples were obtained from the dorsal subcutaneous adipose tissue (ca 1 gram) in the neck region before drug administration, after 1 week of drug administration, and 1 week after withdrawal of drug. Adipose tissue slices were prepared from the biopsy sample, and in vitro lipogenesis was determined with radioactive glucose as substrate. The incubation was similar to that previously described except that there was no DMSO or test compound in the flasks. Compared to the control animals, it was found that neither of the test compounds had significantly affected lipogenesis after 1 week, but Compound 1 and Compound 6 had significantly reduced the lipogenic rate after 2 weeks.

The compounds of Formula I can be used to control lipogenesis in mammals such as, for example, pets, animals in a zoo, livestock, fur-bearing animals and domestic animals, including, but not limited to dogs, cats, mink, sheep, goats, swine, cattle, horses, mules and donkeys. The effect is obtained by administering an effective amount of one or more of the compounds orally or parenterally to the animal. They may be administered as such, or as an active ingredient of a conventional pharmaceutical formulation. They may be administered orally by any convenient means. Thus, they may be administered as a drench, by intubation, in the animal's food and water, in a food supplement or in a formulation expressly designed for administration of the drug. Suitable formulations include solutions, suspensions, dispersions, emulsions, tablets, boluses, powders, granules, capsules, syrups, elixirs. For parenteral administration, they may be in the form of a solution, suspension, dispersion or emulsion. They can be administered in the form of an implant or other controlled sustained release formulation. Inert carriers, such as one or more of water, edible oil, geletin, lactose, starch, magnesium sterate, talc, or vegetable gum can be used. The dosage of the compound of the invention needed to inhibit lipogenesis will depend upon the particular animal being treated. However, in general, satisfactory results are obtained when the compounds are administered in a dosage of from about 1 to about 500 milligrams per kilogram of the animal's body weight. The compound can be administered in a single dose or a series of doses in the same day, or over a period of days. For any particular animal, a specific dosage regimen should be adjusted according to the individual need, the particular compound(s) used as the inhibitor, and the professional judgement of the person administering or supervising the administration of the inhibitor. It is to be understood that the dosages set forth herein are exemplary only, and that they do not, to any extent, limit the scope or practice of the invention.

We claim:

1. A method for inhibiting lipogenesis in a mammal, which comprises administering, to a mammal in need of such treatment, orally or parenterally, an effective lipogenesis inhibiting amount of a compound of the formula:

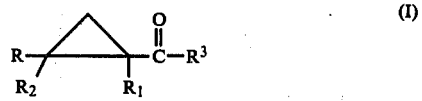

consisting of two subclasses:
(1) R is alkyl having 4 to 10 carbon atoms, acetoxymethyl, or phenyl, $R^1$ and $R^2$ each is hydrogen, or —CN, with the proviso that one of them is hydrogen, and $R^3$ is —$NH_2$, or —$OR^4$, wherein $R^4$ is alkyl having 1 to 4 carbon atoms;
(2) R is alkyl having 6 to 16 carbon atoms, or is phenyl, $R^1$ and $R^2$ each is hydrogen or —CN, with the proviso that one of them is hydrogen and $R^3$ is —OH.

* * * * *